United States Patent [19]

Lin et al.

[11] Patent Number: 4,647,691

[45] Date of Patent: * Mar. 3, 1987

[54] PROCESS FOR PREPARING ETHYL AND N-PROPYL ESTERS OF CARBOXYLIC ACIDS FROM METHANOL, SYNGAS AND CARBOXYLIC ACID USING A NEW CATALYST SYSTEM

[75] Inventors: Jiang-Jen Lin, Round Rock; John F. Knifton, Austin, both of Tex.

[73] Assignee: Texaco Inc., White Plains, N.Y.

[*] Notice: The portion of the term of this patent subsequent to Feb. 1, 2000 has been disclaimed.

[21] Appl. No.: 339,233

[22] Filed: Jan. 13, 1982

[51] Int. Cl.$^4$ .............................................. C07C 67/36
[52] U.S. Cl. ......................... 560/265; 260/410.9 R; 546/321; 546/327; 549/484; 560/1; 560/64; 560/100; 560/103; 560/105; 560/114; 560/122; 560/124; 560/152; 560/155; 560/175; 560/178; 560/226; 560/227; 558/441
[58] Field of Search .............. 560/265, 232, 204, 100, 560/105, 103, 122–124, 114, 152, 187, 175, 178, 226–227, 64, 155; 260/410.9 R, 465.4; 549/484; 546/321, 327; 568/902

[56] References Cited

U.S. PATENT DOCUMENTS

| | | | |
|---|---|---|---|
| 4,133,966 | 1/1979 | Pretzer et al. | 560/265 |
| 4,189,441 | 2/1980 | Braca et al. | 560/265 |
| 4,205,190 | 5/1980 | Gane et al. | 568/902 |
| 4,371,724 | 2/1983 | Lin et al. | 568/902 |
| 4,374,285 | 2/1983 | Lin et al. | 568/902 |
| 4,414,410 | 11/1983 | Lin et al. | 560/265 |
| 4,430,506 | 2/1984 | Gauthier-Lefaye et al. | 560/105 |

*Primary Examiner*—Werren B. Lone
*Attorney, Agent, or Firm*—Jack H. Park; Cynthia L. Kendrick

[57] ABSTRACT

Ethyl and n-propyl esters of carboxylic acids are prepared in good yield from methanol, syngas and a carboxylic acid by contacting a mixture of the carboxylic acid, carbon monoxide, hydrogen and methanol with a catalyst composition comprising a ruthenium-containing compound, a cobalt-containing compound and a quaternary onium salt or base, and heating the resulting mixture at an elevated temperature and pressure for sufficient time to produce the desired ethyl and propyl esters, and then recovering the same from the reaction mixture.

23 Claims, No Drawings

PROCESS FOR PREPARING ETHYL AND N-PROPYL ESTERS OF CARBOXYLIC ACIDS FROM METHANOL, SYNGAS AND CARBOXYLIC ACID USING A NEW CATALYST SYSTEM

BACKGROUND OF THE INVENTION

1. Field of the Invention

This invention relates to a new process for preparing ethyl and n-propyl esters of carboxylic acids. More particularly, the invention relates to a new process for preparing ethyl esters of carboxylic acids from the acids, methanol and syngas using a novel catalyst system.

Specifically, the invention provides a new and improved process for preparing ethyl and n-propyl esters of carboxylic acids, such as ethyl propionate, and n-propyl propinate in good yield from aliphatic carboxylic acids, such as propionic acid, carbon monoxide, hydrogen and methanol, which process comprises contacting a mixture of the carboxylic acid, carbon monoxide, hydrogen and methanol with a catalyst composition comprising a ruthenium-containing compound, a cobalt-containing compound and a quaternary onium salt or base, and heating the resulting mixture at an elevated temperature and pressure for sufficient time to produce the desired ethyl and propyl esters, and then recovering the same from the reaction mixture.

2. Prior Art

Ethyl and n-propyl esters, such as ethyl propionate and n-propyl propionate, are chemicals which have found wide use in industry. They may be used, for example, in the production of anhydrides and in the production of the valuable building blocks, ethylene and propylene. These esters may also be used as solvents and diluents and as softeners for resins.

Various methods have been used in the past for the production of the ethyl esters. The esters can be produced, for example, by reaction of the ethanol with the desired carboxylic acid, both components commonly being obtained from petroleum and agrichemical feedstocks. A direct synthesis of the ethyl esters from syngas would be potentially more economical and highly desirable.

It has been proposed to prepare the ethyl esters of carboxylic acids by carbonylation techniques, but these methods up to the present have not been entirely satisfactory as they give low yields of the desired ethyl esters or use expensive catalysts or catalysts that are difficult to utilize on a large scale. For example, U.S. Pat. No. 4,270,015 and references cited therein disclose various catalyst systems for use in producing ethyl esters by carbonylation. U.S. Pat. No. 4,270,015 discloses the preparation of ethyl esters from syngas using a ruthenium-Group VA ligand catalyst as catalyst. While this process produces the ethyl esters, there is a great deal to be desired as to the selectivity and yield of the desired product.

It is an object of the invention, therefore, to provide a new and improved process for preparing the ethyl and n-propyl esters of carboxylic acids. It is a further object to provide a process for preparing esters, such as ethyl propionate and propyl propionate, from syngas, methanol and a carboxylic acid, such as propionic acid, using a new and improved catalyst system. It is a further object to provide a new process for preparing ethyl and n-propyl esters of carboxylic acids which give improved selectivity and yield. It is a further object to provide a new process for making ethyl and n-propyl esters from syngas using a catalyst system which is suitable for use on large scale operations. These and other objects of the invention will be apparent from the following detailed description thereof.

SUMMARY OF THE INVENTION

It has now been discovered that these and other objects may be accomplished by the process of the invention comprising contacting a mixture of a carboxylic acid, carbon monoxide, hydrogen and methanol with a catalyst composition comprising a ruthenium-containing compound, a cobalt-containing compound and a quaternary onium salt or base, and heating the resulting mixture at an elevated temperature and pressure for sufficient time to produce the desired ethyl and propyl carboxylic acid esters, and then recovering the same from the reaction mixture. It was surprising to find that the new catalyst system using the cobalt-containing compound as cocatalyst in the presence of methanol gives improved selectivity in the formation of the ethyl esters and improved conversion rates. Further advantage is found in the fact that the process utilizes a catalyst system that can be adapted for use on a large commercial scale.

The process of the invention is particularly characterized by the good selectivity in the conversion of the acids and methanol to the desired esters as according to the equation:

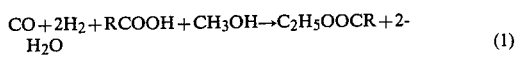

$$CO + 2H_2 + RCOOH + CH_3OH \rightarrow C_2H_5OOCR + 2H_2O \quad (1)$$

Typical conversion of the carboxylic acid ranges from 65% to about 84%, with the total yield of the ethyl and n-propyl esters ranging from 49% to 63%. With the formation of the desired ethyl and propyl esters, other esters, such as methyl and butyl esters are also formed as minor by-products.

DETAILED DESCRIPTION OF THE INVENTION

In the operation of the process of the invention, the ethyl and propyl esters, along with the minor by-products such as the methyl and butyl esters, are produced concurrently from the carboxylic acid, syngas and methanol by a process comprising the following steps:

(a) contacting a mixture of carboxylic acid, carbon monoxide, hydrogen and methanol with a catalyst comprising a ruthenium-containing compound, a cobalt-containing compound and a quaternary onium salt or base, preferably in the presence of a solvent, (b) heating the said mixture to an elevated temperature, e.g. above 150° C. and an elevated pressure, e.g. above 500 psi, with sufficient carbon monoxide and hydrogen to satisfy the stoichiometry of the formation of the esters as noted in equation 1 above, until substantial formation of the desired ester has been achieved, and (c) preferably isolating the said ethyl and propyl esters and minor by-products from the reaction mixture, as by distillation.

In order to present the inventive concept of the present invention in the greatest possible detail, the following supplementary disclosure is submitted. The process of the invention is practiced as follows:

As noted, the new catalyst system used in the process of the invention contains a ruthenium-containing compound, a cobalt-containing compound and a quaternary onium salt or base. The ruthenium-containing compounds employed as a catalyst may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonylruthenium nitrate, or as the salt of a suitable organic carboxylic acid, for example, ruthenium(III) acetate, ruthenium naphthenate, ruthenium valerate and ruthenium complexes with carbonyl-containing ligands such as ruthenium(III) acetylacetonate. The ruthenium may also be added to the reaction zone as a carbonyl or hydrocarbonyl derivative. Here, suitable examples include, among others, triruthenium dodecacarbonyl and other hydrocarbonyls such as $H_2Ru_2(CO)_{12}$, and substituted carbonyl species such as the tricarbonylruthenium(II) chloride dimer, $(Ru(CO)_3Cl_2)_2$.

Preferred ruthenium-containing compounds include oxides of ruthenium, ruthenium salts of an organic carboxylic acid and ruthenium carbonyl or hydrocarbonyl derivatives. Among these, particularly preferred are ruthenium(IV) dioxide hydrate, ruthenium(VIII) tetraoxide, anhydrous ruthenium(IV) oxide, ruthenium acetate, ruthenium propionate ruthenium (III) acetylacetonate, and triruthenium dodecacarbonyl.

The cobalt-containing compound to be used in the catalyst composition may take many different forms. For instance, the cobalt may be added to the reaction mixture in the form of an oxide, salt, carbonyl derivative and the like. Examples of these include, among others, cobalt oxides $Co_2O_3$, $Co_3O_4$, CoO, cobalt(II) bromide, cobalt(II) iodide, cobalt(II) thiocyanate, cobalt(II) hydroxide, cobalt(II) carbonate, cobalt(II) nitrate, cobalt(II) phosphate, cobalt acetate, cobalt naphthenate, cobalt benzoate, cobalt valerate, cobalt cyclohexanoate, cobalt carbonyls, such as dicobalt octacarbonyl $Co_2(CO)_8$, tetracobalt dodecacarbonyl $Co_4(CO)_{12}$ and hexacobalt hexadecacarbonyl $Co_6(CO)_{16}$ and derivatives thereof by reaction with ligands, and preferably group V donors, such as the phosphines, arsines and stibine derivatives such as $(Co(CO)_3L)_2$ wherein L is $PR_3$, $AsR_3$ and $SbR_3$ wherein R is a hydrocarbon radical, cobalt carbonyl hydrides, cobalt carbonyl halides, cobalt nitrosyl carbonyls as $CoNO(CO)_3$, $Co(NO)(CO)_2PPh_3$, cobalt nitrosyl halides, organometallic compounds obtained by reacting cobalt carbonyls with olefins, allyl and acetylene compounds, such as bis($\pi$-cyclopentandienyl) cobalt ($\pi C_5H_5)_2Co$, cyclopentadienyl cobalt dicarbonyl, bis(hexamethylenebenzene)cobalt.

Preferred cobalt-containing compounds to be used in the catalyst system comprise those having at least one cobalt atom attached to carbon, such as the cobalt carbonyls and their derivatives as, for example, dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt dicarbonyl, cobalt carbonyl halides, cobalt carbonyl hydrides, cobalt nitrosyl carbonyls, and the like, and mixtures thereof.

Particularly preferred cobalt-containing compounds to be used in the catalyst comprise those having at least one cobalt atom attached to at least three separate carbon atoms, such as for example, the dicobalt octacarbonyls and their derivatives.

The quaternary onium salt or base to be used in the catalyst composition may be any onium salt or base, but are preferably those containing phosphorus or nitrogen, such as those of the formula

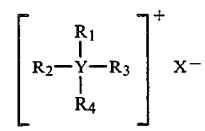

wherein Y is phosphorus or nitrogen, $R_1$, $R_2$, $R_3$ and $R_4$ are organic radicals preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium or ammonium acetates, hydroxides, nitrates, chromates, tetrafluoroborates and other halides, such as the corresponding chlorides, and iodides, are also satisfactory.

Equally useful are the phosphonium and ammonium salts containing phosphorus or nitrogen bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorus or nitrogen through the aryl function.

Illustrative examples of suitable quaternary onium salts or bases include tetrabutylphosphonium bromide, heptyltriphenylphosphonium bromide, tetrabutylphosphonium iodide, tetrabutylammonium chloride, tetrabutyl phosphonium nitrate, tetrabutylphosphonium hydroxide, tetrabutylphosphonium chromate, tetraoctylphosphonium tetrafluoroborate, tetrahexylphosphonium acetate and tetraoctylammonium bromide.

The preferred quaternary onium salts and bases to be used in the process comprise the tetralkylphosphonium salts containing alkyl groups having 1 to 6 carbon atoms, such as methyl, ethyl, butyl, hexyl, heptyl and isobutyl. Tetralkylphosphonium salts, such as the halides, bromides, chlorides and iodides, and the acetate and chromate salts and hydroxide base, are the most preferred.

The quantity of the ruthenium-containing compound and the cobalt-containing compound to be used in the process of the invention may vary over a wide range. The process is conducted in the presence of a catalytically effective quantity of the active ruthenium-containing compound and the active cobalt-containing compound which gives the desired product in a reasonable yield. The reaction proceeds when employing as little as about $1 \times 10^{-6}$ weight percent, and even lesser amounts of the ruthenium-containing compound, together with as little as about $1 \times 10^{-6}$ weight percent of the cobalt-containing compound, or even lesser amounts, based on the total weight of the reaction mixture. The upper concentration is dictated by a variety of factors including catalyst cost, partial pressures of carbon monoxide, operating temperature, etc. A ruthenium-containing compound concentration of from about $1 \times 10^{-5}$ to about 10 weight percent in conjunction with a cobalt-containing compound concentration of from about $1 \times 10^{-5}$ to about 5 percent, based on the total weight of the reaction mixture is generally desirable in the practice of this invention. The preferred ruthenium to cobalt atomic ratios are from about 10:1 to 1:10.

Generally, in the catalyst system used in the process of the invention, the molar ratio of the ruthenium-containing compound to the quaternary onium salt or base will range from about 1:0.01 to about 1:100 or more, and preferably will be from about 1:1 to about 1:20.

Particularly superior results are obtained when the above-noted three components of the catalyst system are combined in a molar basis as follows: ruthenium-containing compound 0.1 to 4 moles, cobalt-containing compound 0.025 to 1.0 moles and the quaternary onium salt or base 0.4 to 60 moles, and still more preferably when the components are combined in the following molar ratios; ruthenium-containing compound 1 to 4 moles, cobalt-containing compound 0.25 to 1.0 moles and the quaternary onium base or salt 10 to 50 moles.

The carboxylic acid used in the process of the invention forms the acid moiety of the desired alkyl ester. Suitable carboxylic acids include the aliphatic acids, alicyclic monocarboxylic acids, heterocyclic acids and aromatic acids, both substituted and unsubstituted. Examples of such acids include, among others, the lower mono aliphatic carboxylic acids, such as formic acid, acetic, propionic, butyric, isobutyric, valeric, caproic, capric, perlargonic and lauric acids, together with polycarboxylic acids, such as oxalic, malonic, succinic and adipic acids. The invention further contemplates the use of substituted monoaliphatic acids containing one or more functional substituents, such as the lower alkoxy, chloro, fluoro, cyano, alkylthio, and amino functional groups, examples of which include acetoacetic acid, dichloroacetic acid and trifluoroacetic acid, chloropropionic acid, trichloroacetic acid, monofluoroacetic acid and the like. Among the suitable aromatic acids contemplated are benzoic acid, naphthoic acids, toluic acids, chlorobenzoic acids, aminobenzoic acids and phenylacetic acid. The alicyclic monocarboxylic acids preferably contain from 3 to 6 carbon atoms in the ring, both substituted or unsubstituted, and may contain one or more carboxyl groups, such as cyclopentanecarboxylic acid and hexahydrobenzoic acids. The heterocyclic acids preferably contain 1 to 3 fused rings both substituted or unsubstituted together with one or more carboxylic acid groups, examples include quinolinic, furoic and picolinic acids. Mixtures of these classes of carboxylic acids, in any ratio, may also be used in the process of the invention. The corresponding anhydrides may also be used.

Preferred carboxylic acids include the lower monocarboxylic acids containing from 1 to 12 carbon atoms, and the halo, alkoxy, cyano, alkylthio and aminosubstituted derivatives thereof, and the dicarboxylic acids containing up to 12 carbon atoms.

The amount of the carboxylic acid and the methanol to be used in the process of the invention may vary over a wide range. In general, the amount of the acid and methanol to be used should be sufficient to satisfy the stoichiometry of the formation of the esters as shown in equation 1 above, although larger or smaller amounts may be used as desired or necessary.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon, and the like, or they may include gases that may, or may not undergo reaction under carbon monoxide hydrogenation conditions, such as carbon dioxide, hydrocarbons, such as methane, ethane, propane, and the like, ethers such as dimethyl ether, methylethyl ether and diethyl ether, and higher alcohols.

Solvents may be and sometimes preferably are employed in the process of the invention. Suitable solvents for the process include the oxygenated hydrocarbons, e.g. compounds possessing only carbon, hydrogen and oxygen and one in which the oxygen atom present is in an ether, ester, ketone carbonyl or hydroxyl group or groups. Generally, the oxygenated hydrocarbon will contain from about 3 to 12 carbon atoms and preferably a maximum of three oxygen atoms. The solvent must be substantially inert under the reaction conditions, must be relatively non-polar and preferably one which has a normal boiling point of at least 65° C. at atmospheric pressure and still more preferably, the solvent will have a boiling point greater than that of the ester and other products of the reaction so that recovery of the solvent by distillation is facilitated.

Preferred ester type solvents are the aliphatic, cycloaliphatic and aromatic carboxylic acid esters as exemplified by methyl benzoate, isopropyl benzoate, butyl cyclohexanoate, as well as dimethyl adipate. Useful alcohol-type solvents include the monohydric alcohols as cyclohexanol and 2-octanol, etc. Suitable ketone-type solvents include, for example, cyclic ketones, such as cyclohexanone, 2-methylcyclohexanone, as well as acyclic ketones, such as 2-pentanone, butanone, acetophenone, etc. Ethers which may be utilized as solvents include cyclic, acyclic, and heterocyclic materials. Preferred ethers are the heterocyclic ethers as illustrated by 1,4-dioxane and 1,3-dioxane. Other suitable ethers include isopropyl propyl ether, diethylene glycol, dibutyl ether, diphenyl ether, heptyl phenyl ether, anisole, tetrahydrofurane, etc. The most useful solvents of all of the above groups include the ethers, as represented by the polycyclic, heterocyclic ethers such as diphenyl ether and 1,4-dioxane, etc.

The amount of the solvent employed may vary as desired. In general, it is desirable to use sufficient solvent to fluidize the catalyst system.

The temperature range which can usefully be employed in the process of the invention may vary over a considerable range depending upon experimental facts, including the choice of catalyst, pressure and other variables. The preferred temperatures are above 150° C. and more preferably between 150° C. and 350° C. when superatmospheric pressures of syngas are employed. Coming under special consideration are the temperatures ranging from about 180° C. to about 250° C.

Superatmospheric pressures of about 500 psi or greater lead to substantial yield of the desired esters. A preferred range is from about 1000 psi to about 7500 psi, although pressures above 7500 also provide useful yields of the desired products. The pressures referred to herein represent the total pressure generated by all the reactants, although they are substantially due to the carbon monoxide and hydrogen reactants.

The desired products of the reaction, the ethyl and n-propyl esters of the desired alkanoic acids, will be formed in significant quantities varying from about 49% to about 63% in yield. Also formed will be minor by-products, such as the methyl, propyl and butyl esters of those alkanoic acids as well as other oxygenated products. The desired products can be recovered from the reaction mixture by conventional means, such as fractional distillation in vacuo, etc.

The process of the invention can be conducted in a batch, semi-continuous or continuous manner. The catalyst can be initially introduced into the reaction zone batchwise, or it may be continuously or intermittently introduced into such a zone during the course of the snythesis reaction. Operating conditions can be adjusted to optimize the formation of the desired esters, and said material can be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures; viz, gas-liquid chromatography (glc), infrared (ir) mass spectometry, nuclear magnetic resonance (nmr) and elemental analyses, or a combination of these techniques. Analyses have, for the most part, being by parts by weight; all temperatures are in degree centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates an improved synthesis of ethyl and propyl propionate from synthesis gas, propionic acid and methanol using the catalyst system comprising the ruthenium-containing compound, a cobalt-containing compound and a quaternary onium salt or base.

A glass liner was charged with ruthenium oxide hydrate (1 mmole, 0.19 g) n-heptyltriphenylphosphonium bromide (10 mmole, 4.25 g), dicobalt octacarbonyl (0.25 mmole, 0.085 g) and 5.2 grams of methanol (0.16 mole) and 12 grams of propionic acid (0.16 mole). The glass liner was placed in a stainless steel reactor and purged of air with hydrogen and carbon monoxide (1:1 ratio), then pressured to 2000 psi and heated to 220° C. The pressure was brought up to 6000 psi and during the reaction period, the constant pressure was maintained by using a surge tank. After 18 hours, the reactor was allowed to cool, the gas pressure (3300 psi) noted, the excess gas vented and the liquid products recovered.

The liquid products (21.8 g) were analyzed by glc as follows:
43 weight percent ethyl propionate
7.9 weight percent n-propyl propionate
4.1 weight percent methyl propionate
3.9 weight percent ethanol
0.4 weight percent unreacted methanol
24.6 weight percent unreaction propionic acid Ethyl and n-propyl propionate selectivities were calculated to be:
ethyl propionate 69 mole %
n-propyl propionate 11 mole %
Total ethyl and n-propyl propionate selectivity = 80 mole %

Ethyl and n-propyl propionate yields, basis on propionic acid charged were calculated to be:
ethyl propionate 45 mole %
n-propyl propionate 7 mole %
Total ethyl and n-propyl propionate yield = 52 mole %
The conversion of propionic acid was 65 mole %.

COMPARATIVE EXAMPLE A

For the purpose of comparison, this example illustrates the synthesis of ethyl and n-propyl propionate using the catalyst comprising ruthenium oxide, n-heptyltriphenylphosphonium bromide, dicobalt octacarbonyl, plus propionic acid and syngas. There is no methanol co-reactant in this comparative example A.

A glass liner was charged with hydrated ruthenium oxide hydrate (0.19 grams, 1.0 mmole), n-heptyltriphenylphosphonium bromide (4.25 grams, 10 mmoles), dicobalt octacarbonyl (0.085 grams, 0.25 mmole) and propionic acid (10.0 grams, 135 mmoles). The glass liner was placed in a stainless steel reactor and purged of air with hydrogen and carbon monoxide (1:1 molar ratio), then pressured to 2000 psi and heated to 220° C. The pressure was brought up to 6280 psi and during the reaction period, the constant pressure was maintained by using a surge tank. After 18 hours, the reactor was allowed to cool, the gas pressure (3950 psi) noted, the excess gas sampled and vented and 16.9 g of the liquid products recovered.

Analysis of the product liquid fraction by gas-liquid chromotography (glc) showed the presence of:
30.3% ethyl propionate
15.6% n-propyl propionate
2.4% methyl propionate
1.9% n-butyl propionate
41.4% unreacted propionic acid Ethyl and propyl propionate selectivities were calculated to be:
ethyl propionate 56 mole % selectivity
n-propyl propionate 25 mole % selectivity
Total ethyl and n-propyl propionate selectivity = 81 mole %

Ethyl and n-propyl propionate yields, based on propionic acid charge, were calculated to be:
ethyl propionate 27 mol %
n-propyl propionate 12 mol %
The total ethyl and n-propyl propionate yield was 39 mol %. Conversion of propionic acid is estimated to be 49 mol %.

It may be noted that:
1. The total yield of ethyl and n-propyl propionate (39 mol %) in the comparative example (A) is lower than the 52 mol % achieved in Example I using methanol as the coreactant.
2. Selectivity to ethyl and n-propyl propionate (81 mol % total) is similar to the figure (80 mol %) achieved in Example I.

EXAMPLE II

A glass liner was charged with ruthenium oxide hydrate (1 mmole, 0.19 g), n-heptyltriphenylphosphonium bromide (10 mmole, 4.25 g), dicobalt octacarbonyl (0.25 mmole, 0.085 g), methanol (162 mmole, 5.2 g) propionic acid (162 mmoles, 12.0 g) and p-dioxane (10.0 g). The glass liner was placed in a stainless steel reactor and purged of air with hydrogen and carbon monoxide (1:1 ratio), then pressured to 2000 psi and heated to 220° C. The pressure was brought up to 6300 psi and during the reactive period, the constant pressure was maintained by using a surge tank. After 18 hours, the reactor was allowed to cool, the gas pressure (3500 psi) noted, the excess gas vented and the liquid products recovered (30.3 g).

The liquid products were analyzed by glc as follows:
30.4 weight percent ethyl propionate
6.2 weight percent n-propyl propionate
3.9 weight percent methyl propionate
2.3 weight percent ethanol
11.4 weight percent unreacted propionic acid
0 weight percent unreacted methanol
34.5 weight percent p-dioxane
Ethyl and n-propyl propionate selectivities were calculated to be:
ethyl propionate 57 mole %
n-propyl propionate 10 mole %
Ethyl and n-propyl propionate yields, based on propionic acid charged, were calculated to be:
ethyl propionate 45 mole %
n-propyl propionate 8 mole %
The conversion of propionic acid was 78%.

EXAMPLE III

Following the procedure of Example I, the synthesis of ethyl and propyl propionate was repeated with the exception that 10 grams of diphenyl ether was included in the reaction mixture as inert solvent. The pressure in the reactor during the desired synthesis was maintained at 6100 psi and the temperature was maintained at 220° C. The liquid product (31.7 g) was recovered at the conclusion of the reaction, and analysis by glc showed the following results:
Ethyl propionate selectivity 67 mol %
n-propyl propionate selectivity 21 mol %
Methyl propionate selectivity 7 mol %
Total ethyl and n-propyl propionate selectivity is therefore 89 mol %. Ethyl and n-propyl propionate yields (based on propionic acid charged) were calculated to be:
Ethyl propionate 48 mol %
Propyl propionate 15 mol %
Propionic acid conversion was 72%.

EXAMPLE IV

Example I was repeated with the exception that the catalyst system contained 1 mmole of ruthenium oxide hydrate (0.19 g), 10 mmole of n-tetrabutylphosphonium bromide (3.4 g) and 1 mmole of cobalt (III) acetylacetonate (0.36 g) and the reaction mixture contained 7.8 g of methanol and 10 g of propionic acid. Pressure was maintained at 6575 psi and the temperature at 221° C. for 18 hours. The liquid product (23.8 g) obtained at the conclusion of the reaction was analyzed and results were as follows:
Ethyl propionate selectivity 52 mole %
n-propyl propionate selectivity 6 mole %
Ethyl propionate yield 44 mole %
n-propyl propionate yield 5 mole %
Total ethyl plus propyl propionate yield = 49 mole %
Propionic acid conversion was estimated to be 84%.

EXAMPLE V

Example I is repeated with the exception that the ruthenium dioxide hydrate is replaced with equivalent amounts of triruthenium dodecacarbonyl, ruthenium acetate and ruthenium(III) acetylacetonate. Related results are obtained.

EXAMPLE VI

Example I is repeated with the exception that the propionic acid is replaced with equivalent amounts of acetic acid. Related results are obtained.

EXAMPLE VII

Example I is repeated with the exception that the cobalt carbonyl is replaced with equivalent amounts of cobalt(II) acetate and cobalt(III) acetylacetonate. Related results are obtained.

What is claimed is:

1. A process for preparing ethyl and propyl esters of carboxylic acids which comprises contacting a mixture of aliphatic or alicyclic mono carboxylic acids, carbon monoxide, hydrogen and methanol with a catalyst composition consisting essentially of an iodide-free ruthenium-containing compound, an iodide-free cobalt-containing compound and an iodide-free quaternary phosphonium salt or base, and heating the resulting mixture to a temperature above 150° C. and a pressure above 500 psi for sufficient time to produce the desired ethyl and propyl ester, wherein the catalyst components are utilized in the following molar ratios: ruthenium-compound 0.1 to 4 moles: cobalt compound 0.025 to 1.0 moles: quaternary phosphonium salt or base 0.4 to 60 moles.

2. A process as in claim 1 wherein the carboxylic acid is an aliphatic monocarboxylic acid containing from 1 to 12 carbon atoms.

3. A process as in claim 1 wherein the ruthenium-containing compound is a member of the group consisting of one or more oxides of ruthenium, ruthenium acetylacetonate, ruthenium salts of carboxylic acids and ruthenium-carbonyl and hydrocarbonyl compounds.

4. A process as in claim 1 wherein the ruthenium-containing compound is a member of a group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate, and triruthenium dodecacarbonyl.

5. A process as in claim 1 wherein the cobalt-containing compound is a member of the group consisting of cobalt carbonyls and derivatives thereof obtained by reacting the carbonyls with a group V donor ligand selected from the group of compounds consisting of phosphines, arsines and stibine derivatives of the formula $(Co(CO)_3L)_2$ wherein L is $PR_3$, $AsR_3$ and $SbR_3$ wherein R is a hydrocarbon radical, and of cobalt carbonyl hydrides, cobalt carbonyl halides, cobalt nitrosyl carbonyls, cycloalkadienyl cobalt carbonyls, cobalt halides, cobalt oxides and cobalt salts of organic carboxylic acids.

6. A process as in claim 1 wherein the cobalt-containing compound is a cobalt compound having at least one cobalt atom linked to at least three separate carbon atoms.

7. A process as in claim 1 wherein the cobalt-containing compound is a cobalt carbonyl.

8. A process as in claim 1 wherein the cobalt-containing compound is cobalt(III) acetylacetonate.

9. A process as in claim 1 wherein the quaternary onium salt or base is an alkylarylphosphonium salt.

10. A process as in claim 9 wherein the phosphonium salt is selected from the group consisting of alkylarylphosphonium bromides, chlorides and chromates.

11. A process as in claim 1 wherein the synthesis of ethyl and propyl esters of carboxylic acids is conducted in the presence of at least one oxygenated hydrocarbon inert solvent.

12. A process as in claim 11 wherein said inert solvent is selected from the group consisting of 1,3-dioxane, 1,4-dioxane, diethylene glycol dimethyl ether, dibutyl ether and diphenyl ether.

13. A process as in claim 1 wherein the reaction is conducted at a temperature from about 180° C. to about 250° C.

14. A process as in claim 1 wherein the process is conducted at a superatmospheric pressure from about 1000 psi to about 7500 psi.

15. A process as in claim 1 wherein the ruthenium-containing compound is ruthenium oxide hydrate.

16. A process as in claim 1 wherein the quaternary onium salt or base is heptyltriphenylphosphonium bromide.

17. A process as in claim 1 wherein the quaternary onium salt or base is tetrabutylphosphonium bromide.

18. A process as in claim 1 wherein the cobalt-containing compound is dicobalt octacarbonyl.

19. A process for preparing ethyl and n-propyl esters of alkanoic acids which comprises contacting an alkanoic acid, carbon monoxide, hydrogen and methanol with a catalytically effective amount of a catalyst consisting essentially of an iodide free cobalt-containing compound, an iodide free ruthenium-containing compound and an iodide free quaternary phosphonium salt or base, wherein the catalyst components are utilized in the following molar ratios: ruthenium compound 0.1 to 4 moles: cobalt compound 0.025 to 1.0 moles: quaternary phosphonium salt or base 0.4 to 60 moles and heating the resulting mixture at a temperature above 150° C. and a pressure above 1000 psi for sufficient time to produce the desired ethyl and n-propyl alkanoate, and recovering the same from the reaction mixture.

20. A process as in claim 19 wherein the ruthenium-containing compound is a ruthenium oxide, cobalt compound is a cobalt carbonyl and the quaternary onium salt or base is an alkylarylphosphonium halide.

21. A process as in claim 1 or 19 wherein the acid is propionic acid.

22. A process as in claim 1 or 19 wherein the acid is acetic acid.

23. A process as in claim 1 wherein the ruthenium-containing compound is triruthenium dodecacarbonyl.

* * * * *